United States Patent [19]

Allen et al.

[11] Patent Number: 5,274,153

[45] Date of Patent: * Dec. 28, 1993

[54] CONTINUOUS PROCESS FOR PREPARING ALUMINUM ALKYLS AND LINEAR 1-OLEFINS FROM INTERNAL OLEFINS

[75] Inventors: Robert H. Allen; Ronny W. Lin; Andrew D. Overstreet, all of Baton Rouge, La.

[73] Assignee: Ethyl Corporation, Richmond, Va.

[*] Notice: The portion of the term of this patent subsequent to Sep. 1, 2009 has been disclaimed.

[21] Appl. No.: 980,026

[22] Filed: Nov. 23, 1992

Related U.S. Application Data

[60] Division of Ser. No. 739,654, Aug. 2, 1991, Pat. No. 5,191,145, Continuation-in-part of Ser. No. 674,104, Mar. 25, 1991, Pat. No. 5,124,465.

[51] Int. Cl.$^5$ .............................................. C07F 5/06
[52] U.S. Cl. ................................... 556/187; 556/190
[58] Field of Search ................................. 556/187, 190

[56] References Cited

U.S. PATENT DOCUMENTS

| | | | |
|---|---|---|---|
| 3,322,806 | 5/1967 | Asinger et al. | 260/448 |
| 3,369,037 | 2/1968 | Johnston | 260/448 |
| 3,509,228 | 4/1970 | Franz et al. | 260/683.2 |
| 3,641,184 | 2/1972 | Smith et al. | 260/683.2 |
| 4,380,684 | 4/1983 | Fowler et al. | 585/328 |
| 4,484,016 | 11/1984 | Maschmeyer | 585/510 |
| 4,918,254 | 4/1990 | Diefenbach et al. | 585/328 |
| 5,144,053 | 9/1992 | Allen et al. | 556/190 |

*Primary Examiner*—Jose' G. Dees
*Assistant Examiner*—Porfirio Nazario
*Attorney, Agent, or Firm*—David M. Bunnell

[57] ABSTRACT

Linear 1-olefins are continuously prepared from internal olefins by (i) continuously feeding internal olefin, isomerization catalyst and tri-lower alkyl aluminum to a reaction zone so as to cause the internal olefin to isomerize to 1-olefins which displace the lower alkyl groups to form a trialkyl aluminum compound in which at least one of the alkyl groups is a linear alkyl derived from the 1-olefin, (ii) continuously removing trialkylaluminum compound from the reaction zone and, thereafter (iii) reacting the trialkyl aluminum compound with a 1-olefin so as to displace the linear alkyl from the trialkyl aluminum compound, thereby forming a linear 1-olefin product which is substantially free of internal olefins.

17 Claims, 2 Drawing Sheets

CONTINUOUS PROCESS FOR PREPARING ALUMINUM ALKYLS AND LINEAR 1-OLEFINS FROM INTERNAL OLEFINS

This application is a division of application Ser. No. 07/739,654, filed Aug. 2, 1991, now U.S. Pat. No. 5,191,145, which is a continuation-in-part of application Ser. No. 674,104, filed Mar. 25, 1991 now U.S. Pat. No. 5,124,465 which is incorporated herein by reference.

BACKGROUND

This invention relates generally to a process for the isomerization of internal olefins and more specifically to a continuous process for the preparation of aluminum alkyls from internal olefins such as mixed internal hexenes or mixed internal octenes. Linear 1-olefins derived from the internal olefins can be recovered from the aluminum alkyls by back-displacement.

Linear 1-olefin compounds such as 1-hexene are useful comonomers with lower olefins to prepare polymers having improved physical properties. The 1-hexene is normally produced as a co-product of olefin production by a variety of well-known processes such as the ethylene chain growth process in which ethylene reacts with lower aluminum alkyls to form higher alkyl aluminum compounds. The higher, $C_4$ to $C_{30}$ or above, alkyl groups are then displaced from the aluminum by, for example, ethylene or 1-butene to form $C_4$ to $C_{30}$ linear 1-olefins which can be separated and recovered. Increasing demand for 1-hexene has produced a need for preparing it as the primary product. Processes for preparing olefins such as by the dehydrogenation of paraffins or the metathesis of other olefins produce mainly internal olefin products which must then be converted to 1-olefins. Asinger et al. U.S. Pat. No. 3,322,806 describe the preparation of primary alcohols from internal olefins by reacting a non-1-olefin with an aluminum lower alkyl in the presence of catalysts which are compounds of zirconium, uranium, vanadium, chromium, thorium, tungsten, and titanium. The catalyst is believed to promote the conversion of internal olefins to 1-olefins which displace the lower alkyl groups of the aluminum alkyl. The aluminum alkyl is then converted to a primary alcohol by oxidation and hydrolysis. Asinger et al. also disclose such an isomerization/displacement process to prepared alcohols in Chemische Berichte 97, pages 2515-2520 (1964). They reported that nickel compounds were inactive. Later, the thesis of Rainer Oberghaus, Technishen Hochschulle, Aachen, (1969) reported a 55 percent yield of a 1-alcohol from i-Bu$_2$ AlR formed by reacting internal olefin and triisobutylaluminum using a nickel(II) acetylacetonate catalyst.

BRIEF SUMMARY

In accordance with this invention there is provided a continuous process for preparing an alkyl aluminum compound from an internal olefin, said processing comprising:

(a) continuously feeding (i) a linear internal olefin containing 4 to about 30 carbon atoms or a mixture of such internal olefins, (ii) a trialkylaluminum, the mole ratio of said linear internal olefins to said trialkyl aluminum being about 1 to 50:1, and (iii) a catalytic amount of an isomerization catalyst to a reaction zone so as to isomerize the internal olefinic double bond to form at least some linear 1-olefin which displaces alkyl groups from said trialkyl aluminum and forms an alkyl aluminum compound wherein at least one of the alkyl groups bound to aluminum is a linear alkyl derived from said linear 1-olefin, (b) continuously removing olefin formed by the displaced alkyl groups and reaction mixture containing said alkyl aluminum compound from the reaction zone.

In another aspect of the invention there is provided a continuous process for making a 1-olefin compound from an internal olefin, said process comprising:

(a) continuously introducing a linear internal olefin containing 4 to about 30 carbon atoms, or a mixture of such internal olefins, and a trialkyl aluminum, in a mole ratio of linear internal olefin to trialkyl aluminum of about 1 to 50:1, into a reaction zone in the presence of a catalytic amount of an isomerization catalyst so as to (i) cause isomerization of the internal olefinic double bond to form at least some linear 1-olefin and to (ii) cause the linear 1-olefin so formed to displace alkyl groups from said trialkyl aluminum and form an alkyl aluminum compound, wherein at least one of the alkyl groups bound to aluminum is a linear alkyl group derived from said linear 1-olefin, and displaced olefin corresponding to said displaced alkyl groups, (b) continuously removing said displaced olefin and reaction mixture containing said alkyl aluminum compound from said reaction zone, and (c) reacting said alkyl aluminum compound with a 1-olefin in a displacement zone so as to displace said linear alkyl from said alkyl aluminum compound and form a free linear 1-olefin compound.

DETAILED DESCRIPTION

Figure 1:
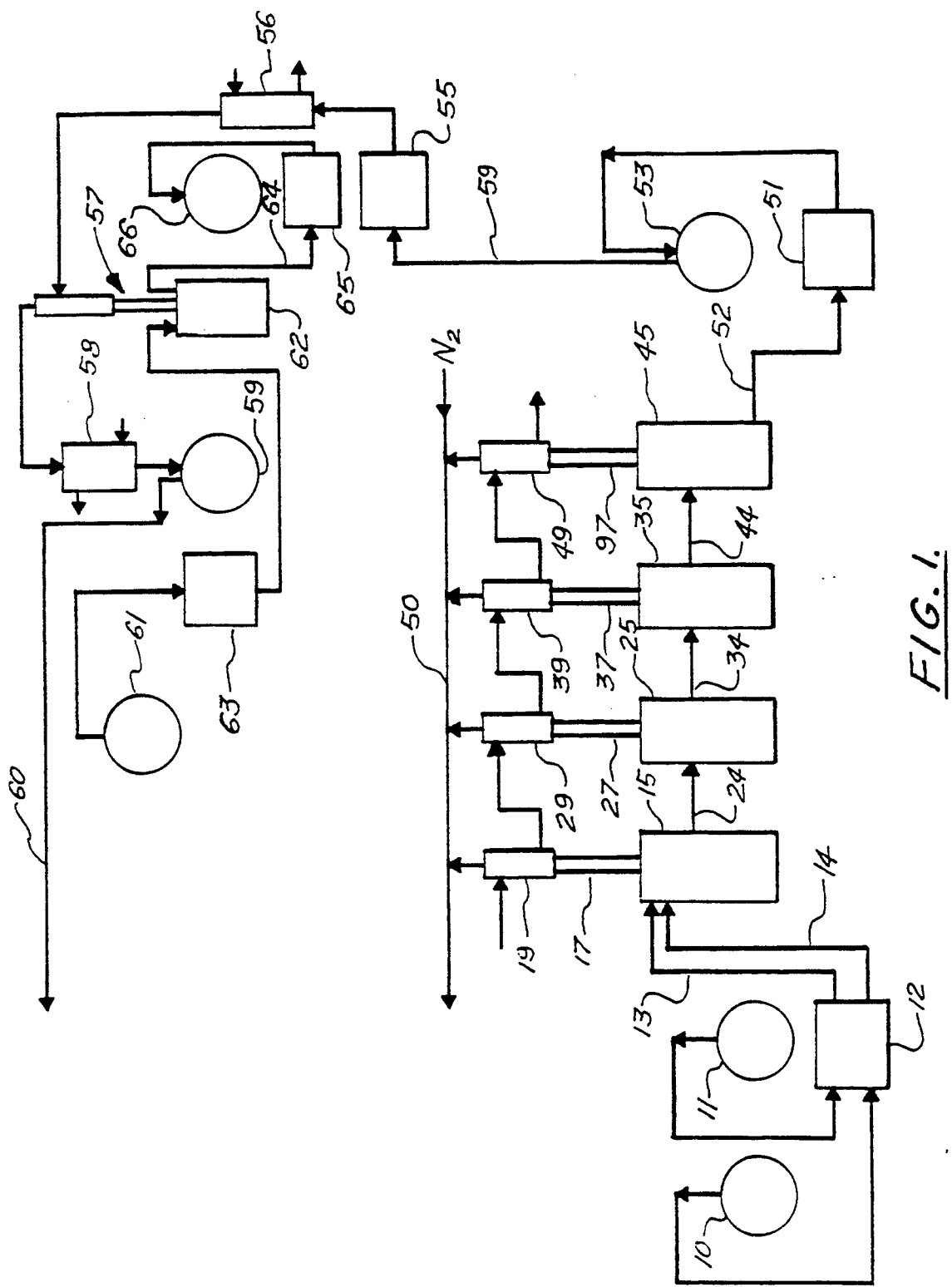
FIG. 1 is a schematic flow diagram illustrating a multi-reactor embodiment of the continuous process of the invention for preparing aluminum alkyls.

The internal olefins which are isomerized in accordance with this invention contain from 4 to about 30 carbon atoms, preferably 4 to 18 carbon atoms and can include mixtures of such olefins. Such internal olefins can be obtained from a number of sources as known in the art. For example, by the dehydration of alcohols or alcohol mixtures, by the metathesis or disproportionation of olefins such as n-butenes to form ethylene, propylene, 3-hexene and 2-pentene, or by the dehydrogenation of $C_4$–$C_{30}$ normal paraffins. Suitable internal olefins include, for example, cis and trans-2-hexene, cis and trans-3-hexene, mixed internal hexenes, mixed internal dodecenes, mixed internal octadecenes and the like.

The alkyl aluminum compounds for the isomerization/displacement process have alkyl groups which, preferably, contain fewer carbons than the predominant carbon number of the internal olefins. In any event, the displaced olefin from the alkyl-aluminum compound should usually have a boiling point below the isomerized olefin because removal of the displaced olefin drives the reaction. However, it is also possible that the displaced olefin can be a vinylidene olefin, in which case thermodynamic equilibria rather than removal of the olefin can drive the reaction. Suitable alkyl aluminum compounds which contain alkyl groups having from 2 to about 20 carbon atoms, preferably 2 to 12 carbon atoms, include, for example, triethylaluminum, tri-n-propylaluminum, tri-n-butylaluminum, triisobutylaluminum, trineohexylaluminum, tri-n-octylaluminum, tri-n-dodecylaluminum, tri-n-octadecylaluminum and the like. Preferred compounds are straight chain alkyl compounds and especially those where the alkyl group does not isomerize upon displacement such as tri-n-propyl aluminum such that the displaced olefin can be easily recycled. Low hydride content aluminum alkyl compounds (less than about 1.0 weight percent and preferably less than about 0.1 weight percent) are required to achieve good yields when using nickel catalysts, because the presence of aluminum hydride impurities rapidly deactivates the catalyst. The $AlH_3$ or $R_2AlH$ content can be reduced by contacting the aluminum alkyl with a 1-olefin such as propylene.

Suitable catalysts for isomerization of the internal olefins include, for example, alkali metals such Na or Li on $Al_2O_3$; Pd, Ni, or Pt on inert supports such as carbon; La on $SiO_2$—$Al_2O_3$; cobalt halide-ligand complexes, e.g. $CoBr_2 \cdot 2P(cyclohexyl)_3$, metal oxides, metal amides, and the like. Preferred catalysts are those which catalyze both isomerization and displacement, for example, titanium and zirconium compounds such as $Ti(O-Bu)_4$ and $Zr(Obu)_4$, and the like. Especially preferred are nickel-containing compounds which are effective isomerization/displacement catalysts to provide yields of aluminum alkyls from internal olefins of about 60 to 90 percent or more. Such nickel compounds include, for example, nickel(II) salts; nickel(II) carboxylates, nickel-(II) acetonates and nickel(0) complexes. Examples of nickel(II) salts include nickel halides, e.g., nickel chloride, nickel bromide, nickel iodide, and their hydrates and the like. Also useful are nickel(II) oxide, nickel(II) hydroxide and the like.

Nickel carboxylates can be represented by the formula:

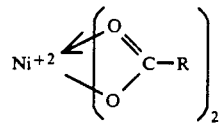

where R is hydrogen or $C_1$-$C_{16}$ alkyl; aryl, i.e. phenyl, naphthyl; substituted aryl, i.e. phenyl and naphthyl substituted with one or more of $C_1$-$C_{16}$ alkyl, halogen (Cl, Br, I, F), and/or haloalkyl etc; aralkyl, i.e. benzyl, naphthobenzyl; and substituted arylalkyl where the aryl group is substituted as described above for substituted aryl, and the like.

Examples of nickel carboxylates include nickel acetate nickel 2-ethylhexanoate, nickel octanoate and nickel naphthenate Nickel acetonates such as acetylacetonate can be represented by the formula:

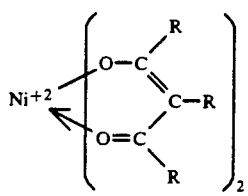

when R is as defined above for the nickel carboxylates.

The foregoing three types of Ni(II) catalysts are believed to be reduced to Ni(0) compounds in the presence of aluminum alkyl/olefin mixtures and form complexes with the olefin which catalyze the isomerization-displacement reaction.

Examples of Ni(0) complex catalysts include $Ni(CO)_4$ and Ni(0) olefin complexes such as nickel bis-1,5-cyclooctadiene ($Ni(COD)_2$), $Ni(C_2H_4)_3$, $Ni(norbornene)_3$, nickel cyclododecatriene and the like. Other Ni(0) catalysts are nickel compounds which are complexed with a ligand such as a trivalent phosphorous compound. The ligand acts to improve the storage stability of catalysts such as $Ni(COD)_2$.

Examples of specific ligand compounds include triphenylphosphine, triethylphosphine, triethoxyphosphine, cyclohexylphosphine, $P(SiMe_3)_3$, and the like.

Examples of specific Ni catalyst-ligand complexes include $Ni(PPh_3)_4$, $Ni(PEt_3)_4$ and $Ni(P(OEt)_3)_4$, each of which are commercially available, and $Ni((Me_2PCH_2)_2)_2$, $Ni(P(SiMe_3)_3)_3$, $Ni(COD)_2 \cdot (cy_2PCH_2)_2$ (where cy=cyclohexyl), $Ni(COD)_2 \cdot (Me_2PCH_2)_2$, $Ni(COD)_2 \cdot P(O\text{-}o\text{-}tolyl)_3$ with $Ni(COD)_2 \cdot Pcy_3$ being preferred. The catalyst complexes can be formed by mixing the nickel compound such as $Ni(COD)_2$ with the desired phosphine in a P/Ni mole ratio of at least 2 for monodentate phosphines at least 1 for the bidentate phosphine ligands. Most nickel(0) phosphine ligands are prepared by reduction of a nickel(II) salt in the presence or a phosphine ligand or by mixing the phosphine with a nickel-olefin complex.

Mixtures of any of the above mentioned catalysts can also be used. Separate catalysts can be used for isomerization and displacement provided that they do not interfere with each other. Examples of displacement catalysts include, for example, colloidal Ni, Pt, Co, nickel acetylacetonate, cobalt carboxylates, e.g. cobalt naphthenate or cobalt acetate, nickel carboxylates, e.g. nickel naphthenate and the like.

The mole ratio of internal olefin to trialkylaluminum can vary and preferably ranges from about 1-50:1 with 5-20:1 preferred and about 10:1 most preferred. Catalytic amounts of nickel catalyst which are effective in the isomerization/displacement process generally range from about 0.01 to 5.0 mole percent of the trialkyl aluminum and preferably about 0.02 to 1.0 mole percent.

According to the continuous isomerization/displacement process, the catalyst is preferably mixed with a portion of the internal olefins to form a first feed solution. The trialkyl aluminum is mixed with a second portion of the internal olefins to form a second feed solution. The feed rates to the reaction zone are adjusted to provide the desired relative proportions of catalyst and reactants. Alternatively, the compositions of the solutions can be selected to provide an approximately equal flow of each feed solution. In order to favor the replacement of the alkyl groups by the isomerized olefins and drive the reaction to high conversion, the displaced alkyl groups in the form of their corresponding 1-olefins are continuously removed as vapor from the reaction mixture and in one embodiment of the invention are used in the recovery of the desired 1-olefins by back-displacement. Unreacted internal olefins are separated from the reaction mixture by distillation or vacuum stripping and returned to the isomerization/displacement reaction zone. The stripping process can be carried out in a batch or continuous manner. Suitable reaction temperatures range from about −20° to 200° C., preferably about 30° to 100° C. Suitable reaction pressures range from about 0 to 100 psia, preferably about 1 to 45 psia and reaction times usually range from about 0.1 to 2 hours. The feed rate and the rate of withdrawal of reaction mixture from the reaction zone ar adjusted to provide the desired residence time.

The reaction zone can include one or more individual reactors in series. Catalyst can be added to the first reaction only or, when a plurality of reactors are used, it can be added to one or more of the additional reactors. The embodiment of the continuous process invention using a series of stirred tank reactors with continuous removal of displaced olefin from each reactor has been found to provide lower concentrations of displaced olefin in the reaction mixture than when a single reactor is used while minimizing back-displacement. This facilitates the conversion of the internal olefin to corresponding n-alkyl groups which are attached to aluminum.

According to the embodiment of the process of the invention for preparing linear 1-olefins, the n-alkyl groups from the isomerized internal olefins are back-displaced from the trialkyl aluminum compounds formed in the isomerization/displacement reaction. A suitable displacement process is described, for example, in U.S. Pat. No. 4,918,254 whose teachings are incorporated herein by reference. The back-displacement can be carried out in a variety of reactor configurations. In a particularly advantageous and novel embodiment, the back-displacement is carried out continuously in a plug flow tubular or packed column reactor with the product 1-olefin flashed from the reaction mixture at low temperatures in order to minimize isomerization.

As described above, the displaced 1-olefin recovered from the isomerization/displacement reaction can preferably be used as the olefin to back-displace the linear 1-olefin from the aluminum alkyl. The regenerated trialkyl aluminum can then be recycled to the isomerization/displacement reaction. However, a different olefin can be used for back-displacement and 1-olefins having from 2 to about 18 carbon atoms including mixtures thereto are especially suitable. The back-displacement can be accomplished without a catalyst but is preferably carried out in the presence of a displacement catalyst. The nickel catalysts which are carried over from the isomerization/displacement step can be effective to catalyze the back-displacement even though they have become inactive in catalyzing the isomerization/displacement reaction. The catalysts are apparently reactivated in the presence of the displacing olefin and heat, for example temperatures above about 40° C. and, preferably 40°-80° C. Fresh catalysts can also be added. Preferred catalysts are those which have the least isomerization activity under the conditions used and include, for example, cobalt carboxylates such as cobalt naphthenate and the like. Nickel complexes, for example, nickel acetylacetonate, nickel carboxylates such as nickel naphthenate, nickel octanoate and nickel acetate, are suitable if used in combination with Pb or Pb compounds to prevent isomerization. Although the cobalt catalysts are about 10 times less active for isomerization than the nickel catalysts, they are preferably also used in connection with Pb or Pb compounds. Cyclodienes and acetylene hydrocarbons, such as phenyl acetylene, can also be used in the displacement reaction to suppress isomerization activity and prolong catalyst life. Effective amounts of catalyst depend upon the catalyst used. Generally amounts of from about 1 to 100 parts per million based on the weight of the reaction mixture can be used and, preferably about 5-50 ppm. Reaction temperatures of from about −20° to 100° C. are suitable for catalyzed displacement. The aluminum alkyl feed to be back-displaced can be treated with a 1-olefin to remove any aluminum hydride so as to extend catalyst life. Higher temperatures of about 300° C. or above may be needed for thermal displacement without catalysts.

The amount of 1-olefin fed to the displacement reaction should be in stoichiometric excess over the amount required to replace all alkyl groups. Preferably the amount of 1-olefin should be at least a 200 percent excess over the stoichiometric amount required to replace all alkyl groups. Still more preferably the 1-olefin feed should be at least a 500 percent stoichiometric excess over the trialkyl aluminum feed stream. In this manner, since the displacement reaction is an equilibrium reaction, the alkyl substitution in the trialkyl aluminum product will more closely approach the distribution of the 1-olefin feed.

Both displacement and side reactions (e.g. isomerization, dimerization, chain growth) proceed concurrently. However the displacement reaction rate is much higher than the rate of the side reactions. This permits termination of the displacement reaction after a time that allows it to go substantially toward the equilibrium conversion and before a time in which the side reactions, especially isomerization, become significant. By "significant" is meant the amount of undesired by-products which would render the olefin effluent stream unsuitable for its intended purpose. In general, the 1-olefin product should contain less than 25 weight percent newly formed combined internal, tri-substituted vinylidene olefins and paraffins. The preferred 1-olefin product is at least 80 weight percent vinyl 1-olefin and more preferably at least 90 weight percent vinyl 1-olefin based on the tri-n-alkylaluminum converted. The process is capable of making 1-olefin product that is over 97 weight percent vinyl 1-olefin based on tri-n-alkylaluminum converted.

Since all rates vary with temperature and amount of catalyst, the optimum time for termination under each specific condition will require a minimal amount of experimentation. In general when operating at 25° C., the reaction should be terminated after a reaction period of about 30 seconds to 1 hour. A preferred reaction time is 1–20 minutes and most preferred 2–5 minutes. At higher temperatures, e.g. 50°–100° C., the preferred reaction time before side reactions become significant will be shorter.

In using a nickel displacement catalyst, when the displacement has proceeded to the desired extent, usually close to reaction equilibrium, a catalyst poison can be added in an amount that will deactivate the nickel catalyst and prevent undesirable side reactions. These poisons include lead and copper and compounds thereof. Suitable lead compounds are lead naphthenate, lead acetylacetonate, lead 2-ethylhexanoate, tetraethyl lead, etc. Suitable copper compounds are copper naphthenate, copper acetylacetonate, cuprous bromide, cuprous 2-ethylhexanoate and the like. Use of the metals as the catalyst poison requires the metals to be in very finely divided forms and requires a greater amount of the catalyst poison. For example, amorphous lead metal is an effective catalyst poison at a Pb/Ni atom ratio of about 500. The catalyst poisons which are effective at the lowest concentrations have been lead compounds, e.g. lead naphthenate, lead 2-ethylhexanoate and lead acetylacetonate.

The amount of catalyst poison should be an amount that effectively inhibits all undesired side reactions.

With lead compounds a lead/nickel atom ratio of 1.0 has been effective and even lower amounts may be effective. Hence a useful Pb/Ni atom ratio is about 0.5/1.0 to 5.0/1.0.

After the catalyst poison has been added, the trialkyl aluminum product can be recovered by conventional methods such a distillation. When lead compounds are used as the poison, nickel and at least part of the lead form a precipitate which can be removed by filtration.

Isomerization during back-displacement can also be suppressed by the addition of an isomerization suppressing amount, preferably, from about 1.0 to 5.0 grams per milligram of nickel in the catalyst, of a cyclodiene compound such as a cyclooctadiene, cycloheptatriene or 1,3-cyclohexadiene and, preferably 1,5-cyclooctadiene. Although small amounts of such cyclodienes favor isomerization, the use of at least about 1.0 gram of cyclodiene per milligram of nickel in the back-displacement reaction, produces a vinyl olefin product which has a reduced isomer impurity content. Unlike lead, the cyclooctadiene can be easily recovered for reuse. This avoids the need to remove added lead and inactivated nickel catalyst by filtration prior to recycling the aluminum alkyl to the isomerization/displacement reaction. Isomerization is also suppressed by acetylenic compounds.

In FIG. 1 an embodiment of the process of the invention for continuously preparing aluminum alkyls from internal olefins is schematically illustrated in which the reaction zone is made up of four stirred tank (back-mix) reactors each of which is equipped with a stirrer, temperature indicator, heater, Vigreux Column and liquid cooled condenser.

According to the process, a trialkyl aluminum-internal olefin mixture is continuously fed from source 10 by duel head peristaltic pump 12 into reactor 15 through line 14. An internal olefin-catalyst mixture is continuously fed from source 11 by pump 12 into reactor 15 through line 13. The feed rate of each solution is controlled by adjusting the pumping rates. Reaction mixture from reactor 15 is continuously removed through line 24 and introduced into reactor 25. The inlet and outlet of line 24 are located beneath the liquid level in each reactor. Similarly reaction mixture from reactor 25 is transferred to the third reactor 35 through line 34 and to the fourth reactor 45 through line 44. The liquid transfer lines are located beneath the liquid level to avoid the transfer of vapor between reactors so that reflux will occur in each reactor.

The liquid level in the system is controlled by positive displacement pump 51 which removes reaction product mixture containing the alkyl aluminum product through line 52 to holding tank 53. In each reactor, internal olefin is isomerized to 1-olefin which displaces the alkyl groups of the feed alkyl aluminum and releases them as the corresponding 1-olefin. This 1-olefin is removed from each reactor as a vapor through reflux columns 17, 27, 37 and 47 and liquid cooled condensers 19, 29, 3 and 49 and collected in line 50 where it is carried by a nitrogen purge to prevent air from entering the system. The displaced 1-olefin can either be discharged through a bubbler or collected and fed to the back-displacement process step when it is desired to recover free 1-olefin corresponding to the internal olefins from the product trialkylaluminum. The alkylaluminum product in tank 53 is pumped through line 54 by positive displacement pump 55 to preheater 56 and then to the top of Oldershaw Column 57 where unreacted internal hexenes are removed as overheads. The internal hexenes are liquified in condenser 58 and collected in tank 59 from which they can be returned through line 60 to the makeup feed for the isomerization/displacement reaction zone through line 60. Cyclohexane from supply 61 is pumped to the reboiler 62 of Oldershaw Column 57 by peristaltic pump 63 at a rate so as to maintain the reboiler bottoms at the desired temperature. The application of vacuum, for example from about 10–100 mm Hg, may be used instead of an inert volatile chaser (cyclohexane) to maintain the temperature at the desired levels. The stripped alkyl aluminum product collects in reboiler 62 and is pumped through line 64 by peristaltic pump 65 to stripped alkyl tank 66.

The process for preparing aluminum alkyls in the above system is further illustrated by but is not intended to be limited to, the following examples.

EXAMPLES 1–3

Preparation of Isomerized Hexenes

Into a 100-gallon Pfaudler glass-lined reactor equipped with an overhead condenser are added 421 lb. of 1-hexene, 4.21 lb. of tri-n-hexyl aluminum, and 38 grams of 8 percent nickel octanoate in mineral spirits. The chemicals are added in an anhydrous and air-free manner and a nitrogen blanket is added to the reactor to prevent the entry of air. The reactor was then heated to 60° C. and maintained at that temperature for two days.

At the end of two days, the 1-hexene is converted into an equilibrium mixture of linear hexenes as evidenced by gas chromatography (approximate composition: 2 percent 1-hexene; 18 percent cis-2-hexene; 57 percent trans-2-hexene; 3 percent cis-3-hexene; 20 percent trans-3-hexene). The reaction mass is then distilled to recover the hexenes overhead. The residual aluminum alkyls and other organics remaining in the reactor are carefully treated with 2N $H_2SO_4$ and then the aqueous layer is neutralized and discarded. The remaining organics in the reactor are incinerated. About 309 lbs. of an equilibrium mixture of linear hexenes are recovered overhead.

This equilibrium mixture of linear hexenes (henceforth hexenes) is used as feed for the isomerization-displacement reactions. These hexenes are stored over Zeolite 3A and kept under a nitrogen pad until use.

Treatment of Aluminum Alkyls

Tri-n-propyl aluminum (TNPA) is treated to remove residual hydride. Approximately 100 g of tri-n-propyl aluminum is combined with approximately 100 g of 1-hexene in a 500-cc round-bottom flask equipped with a magnetically-coupled stirring bar, heating mantle, and reflux condenser. The condenser is maintained at about 0° C. with an aluminum-alkyl-compatible heat transfer fluid such as a 2 centistoke polyalphaolefin. The contents of the flask are heated to reflux for one hour and then are cooled and vacuum-stripped to remove the 1-hexene. Analysis of the tri-n-propyl aluminum typically showed that it contained 5–15 percent hexyl groups following the treatment. This treated tri-n-propyl aluminum (henceforth, TNPA) is used in the isomerization/-displacement reaction experiments.

The continuous isomerization/displacement process illustrated in FIG. 1 is used in preparing tri-n-hexyl aluminum from the isomerized hexene mixture and tri-n-propyl aluminum described above. The reactors are 50 cc, magnetically stirred round-bottom flasks equipped with heating mantles and 12 inch Vigreux Columns. A cold heat-transfer fluid compatible with aluminum alkyls (e.g. polyalphaolefins) is pumped through the condensers at about 0° C. The apparatus is purged with dry nitrogen before operation and during operation there is a cross-purge of nitrogen to prevent air from entering the apparatus.

The first reactor in the series is fed with two 65.6 weight percent hexenes, 29.6 weight percent TNPA, and 4.8 weight percent cyclooctane which serves as an internal standard for gas chromatography. Solution 2 contains hexenes spiked with 38 ppm of Ni in the form of Ni octanoate (10 percent Ni in xylene). The volumetric flows of both solutions to the first flask are approximately equal so that the mole ratio of hexenes to TNPA is about 10.6 to 12.5 and the concentration of Ni between 20-23 ppm regardless of the overall feed rate. During feeding, the contents of all four reactors are brought to reflux with stirring and the total volume of all four reactors held constant at 110 cc by pumping out the contents of the fourth reactor with the second peristaltic pump.

By varying the flow rates of the pumps, overall residence time of the liquid feed in the apparatus is varied between 23 and 65 minutes. During these residence times, the TNPA reacts with the hexenes in the flasks to form tri-n-hexyl aluminum and propylene. The propylene is driven overhead by reflux and vented. The conversion of TNPA to tri-n-hexyl aluminum of the effluent from the fourth reactor varies between 77 and 89 percent.

The results of three runs (Examples 1-3) at steady state for the first three reactors are listed in Table 1. Steady state conversions for the fourth reactor are extrapolated in each case due to exhaustion of the TNPA supply when approximately 92 percent of theoretical response in the last steady state was reached.

TABLE I

| Result or Condition | Example 1 | Example 2 | Example 3 |
|---|---|---|---|
| Absolute Conversion (%) | | | |
| Entering | 13.7 | 13.7 | 13.7 |
| Reactor 1 | 70 | 47 | 54 |
| Reactor 2 | 85 | 65 | 71 |
| Reactor 3 | 89 | 72 | 79 |
| Reactor 4 | 90 | 77 | 80 |
| Normalized Conversion (%) | | | |
| Entering | 0 | 0 | 0 |
| Reactor 1 | 65 | 40 | 46 |
| Reactor 2 | 83 | 59 | 66 |
| Reactor 3 | 88 | 68 | 74 |
| Reactor 4 | 89 | 73 | 77 |
| Temperatures (°C.) | | | |
| Reactor 1 | 69 | 67 | 68 |
| Reactor 2 | 69 | 68 | 69 |
| Reactor 3 | 69 | 68 | 68 |
| Reactor 4 | 68 | 67 | 68 |
| Theo. Approach to SS (%) | | | |
| Reactor 1 | 100.00 | 99.99 | 99.91 |
| Reactor 2 | 99.95 | 99.99 | 99.31 |
| Reactor 3 | 99.73 | 99.91 | 99.61 |
| Reactor 4 | 98.99 | 99.61 | 92.12 |
| Reactor Productivity (lb. Hexene/gal-hr) | | | |
| Through Reactor 1 | 2.25 | 4.37 | 3.38 |
| Through Reactor 2 | 1.42 | 3.25 | 2.42 |
| Through Reactor 3 | 1.01 | 2.48 | 1.82 |
| Through Reactor 4 | 0.76 | 2.00 | 1.41 |
| Reactor vol. (mL) | | | |
| Total | 110 | 110 | 110 |
| Per Reactor | 27.5 | 27.5 | 27.5 |
| Times (min) | | | |
| Total Res. Time | 65 | 23 | 34 |

TABLE I-continued

| Result or Condition | Example 1 | Example 2 | Example 3 |
|---|---|---|---|
| Res Time Per Reactor | 16.2 | 5.8 | 8.6 |
| Total Run Time | 163 | 65 | 60 |
| No. of Res. Times | 2.5 | 2.8 | 1.8 |
| Ni Conc. (ppm wt) | 23 | 20 | 21 |
| Hexene/TNPA Ratio | 12.5 | 10.6 | 10.8 |

EXAMPLE 4

Reaction mass from Example 3 is continuously stripped to separate the internal hexenes from aluminum alkyls as illustrated in the stripping portion of the flow diagram in FIG. 1.

Reaction mass is fed with a spared FMI positive displacement pump through a 12-inch preheater jacketed with 100° C. 2-centistoke polyalphaolefin into the top of a vacuum-jacketed 19 mm 5-stage Oldershaw Column. The flow rate is varied between 1.5 and 3.0 mL/min. A voltage regulator on a 50 cc Glass-Coil heating mantle around the reboiler of the Oldershaw Column is set at 90 percent and cyclohexane is fed to the reboiler with a peristaltic pump at such a rate as to maintain the reboiler bottoms temperature at 100° C., 125° C., or 150° C. The cyclohexane feed rates are 3.0, 1.5, and 0.6 mL/min., respectively. The volume in the reboiler is maintained at 18 mL by continuously pumping out the stripped alkyls with a peristaltic pump. During this process, internal hexenes in the feed are stripped overhead and collected and stripped aluminum alkyl product collects in the reboiler.

The reboiler compositions are as follows:

| Cyclohexane Rate (mL/min) | Temperature °C. | Internal Hexenes in Stripped Alkyl |
|---|---|---|
| 3.0 | 100 | nil |
| 1.5 | 125 | 6.6% |
| 0.6 | 150 | 1.8% |

There is no evidence of decomposition to aluminum metal during continuous stripping experiments.

This Example shows that it is possible to strip the product from Example 3 in a continuous manner to remove most or all of the internal hexenes from the aluminum alkyl without decomposition to aluminum metal and without the application of vacuum. This is accomplished by use of a stripping agent, in this case, cyclohexane, to provide stripping action to remove the internal hexenes overhead. Use of a stripping agent also obviates the need to use excessive heat or vacuum to remove the hexenes.

EXAMPLES 5-7

A continuous isomerization/displacement is carried out using a single stirred tank reactor which was similarly equipped to those used in Examples 1-3. The nickel catalyst (10 percent Ni 2-ethyl hexanoate in xylene) is pumped by a catalyst syringe pump to the internal hexene feed line and the internal hexene-catalyst mixture is continuously pumped into the reactor. Tri-n-propyl aluminum is also continuously pumped to the reactor. Product aluminum alkyl is continuously removed from the reactor. The displaced propylene is removed at the top of the condenser and vented through a nitrogen purge line. Steady states are achieved in each example. The catalyst concentration is varied from 18 to 101 ppm nickel. A summary of conditions and results is given in Table II. In order to allow the system to relax, 3.5 τ (residence time) are allowed.

TABLE II

| Example | Temp. (°C.) | Ni Conc. | Flows (mL/min) Hexene | TPA | Molar Ratio | Residence Time (min) | SS Corrected Conversion |
|---|---|---|---|---|---|---|---|
| 5 | 63° C. | 201 ppm | 2.13 | 0.33 | 9.2 | 13.7 | 50.8% |
| 6 | 64° C. | 18 ppm | 2.10 | 0.33 | 8.9 | 12.8 | 40.1% |
| 7 | 64° C. | 38 ppm | 2.10 | 0.33 | 8.9 | 12.8 | 45.3% |

Figure 2:
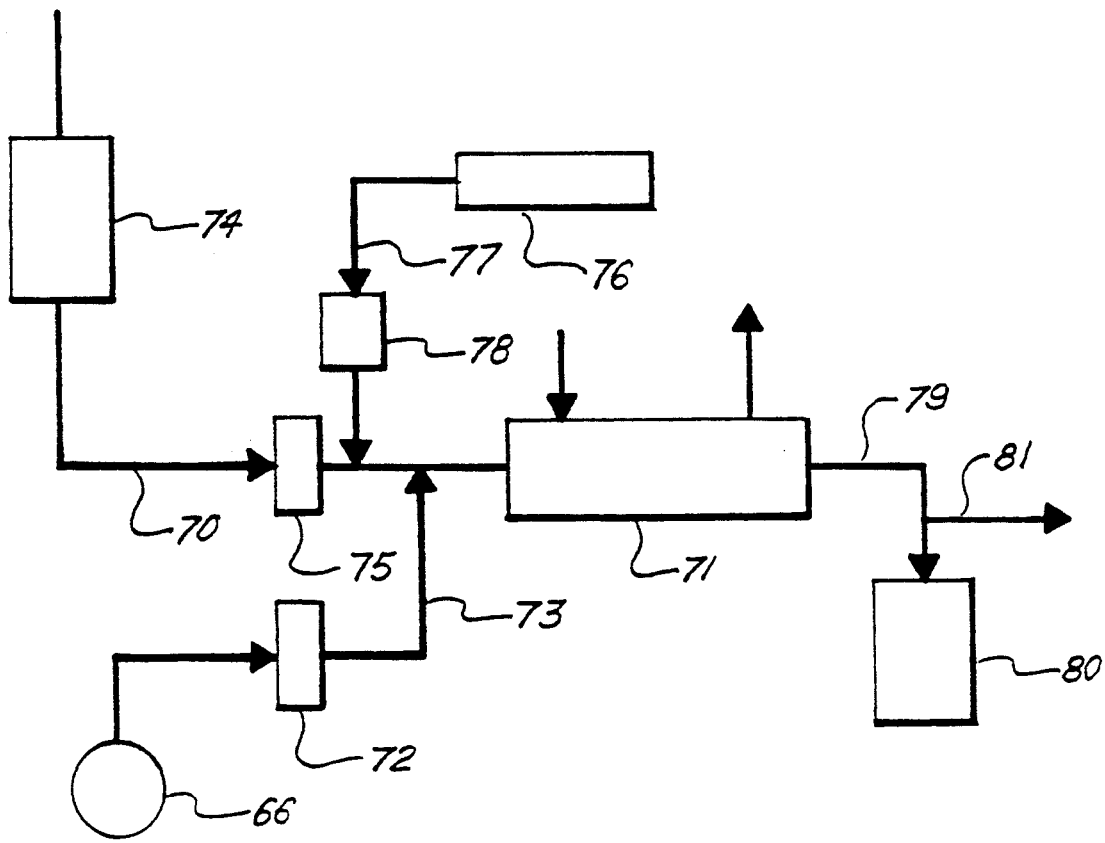
FIG. 2 is a schematic flow diagram illustrating an embodiment of a continuous back-displacement step of the process of the invention.

In FIG. 2, an embodiment of the continuous back-displacement process for recovering 1-alkenes from the aluminum alkyls prepared in the isomerization/displacement step using a catalyst is schematically illustrated. The illustrated embodiment employs a plug flow displacement reaction which is carried out in tubular reactor 71 which is equipped with a jacket to provide temperature control such as by a polyalphaolefin (PAO) liquid bath. Stripped alkyl aluminum product from tank 66 is fed to reactor 71 through lines 73 and 70 by metering pump 72. The product is pretreated to remove any aluminum hydride formed in the stripping step which would poison the catalyst. The 1-olefin for the displacement reaction is fed to reactor 71 through line 70 by metering pump 75. The catalyst solution is fed from supply 76 to reactor 71 through lines 77 and 70 by pump 78. The 1-olefin feed displaces the product 1-olefin in reactor 71 and the excess 1-olefin, the product 1-olefin, and displaced alkyl aluminum exit from reactor 71 through line 79. The excess displacing olefin and product 1-olefin are separated from the bottom stream containing the back-displaced alkyl aluminum which is collected in tank 80. The product 1-olefin and excess olefin exit through line 81. The product 1-olefin is separated from the excess displacing olefin which can be recycled to the displacement reactor. The back-displaced alkyl aluminum can be recycled to the isomerization/displacement reaction with a purge used to remove deactivated Ni catalyst impurities. When a lead kill is used to deactivate the catalyst after the reaction mixture exits from the displacement reactor, the nickel and lead are removed by filtration. In a suitable system for a lead kill process, the lead solution and reaction mixture are fed to a mixing tee, the mixture is filtered and then passed through a jacketed, packed tubular reactor prior to separation of the olefins from the residual aluminum alkyl.

EXAMPLE 8

A continuous back-displacement process of 1-hexene from a hexylaluminum product was carried out as follows. The reaction mass from Example 4 was upgraded with 1-hexene, (50/50 weight ratio), at gentle reflux, (70° C.), for one hour. The solution was allowed to cool and volatiles were partially removed under vacuum for one hour. The solution was then further stripped with a nitrogen purge overnight. Gas chromatography analysis of the upgraded stripped alkyl aluminum showed no internal hexenes and 0.3 percent residual 1-hexene based on hexyl groups and 1-hexene. The alkyl aluminum was upgraded, according to this process, in order to remove aluminum hydrides which would deactivate the displacement catalyst.

The resulting TNHA and liquid propylene were fed into the reactor via metering pumps. Nickel in the form of 10 percent by weight Ni octanoate in mineral spirits and nonane was fed to the reactor via a syringe pump. The reactor consisted of a ¼ inch diameter stainless steel tube, 24 inches in length, which was jacketed with a PAO bath to provide a constant temperature o 25° C. The reaction solution was sampled directly after the reactor.

Flow rates were varied to achieve the following conditions:

| | |
|---|---|
| Propylene/Aluminum = Alkyl mole ratio | 6.7 |
| Residence time in reactor = | 5.2 minutes |
| ppm Ni in reaction solution = | 22 |

The reactor and propylene feed tank were kept at a constant pressure of 180 psi with a nitrogen blanket. All reactants were in the liquid phase. The reaction solution was sampled using a 6 port 2-way valve. The sample loop was in line with the reactor or with the nitrogen/heptane purge. The sample loop was washed with heptane into the sample vial to insure that all reactants were collected. The samples were immediately hydrolyzed with 2N HCl. A gas chromatograph run on the organic phase was used to determine the percent conversion of hexyl groups to 1-hexene.

A 65 percent conversion of hexyl groups to 1-hexene resulted. There were less than 0.5 percent by weight internal hexenes formed. This example demonstrates that the upgraded TNHA from Example 4 can undergo back-displacement with propylene and Ni catalyst to form very pure 1-hexene and TNPA.

EXAMPLE 9

The back-displacement reaction was undertaken as in Example 8 except the reaction was run at atmospheric pressure, 1-octene was used as the displacing olefin and a lead kill was used to deactivate the catalyst after displacement. The nickel (TNHA) used was Ethyl TNHA which had been treated with 1-hexene as described in Examples 1-3 under the heading "Treatment of Aluminum Alkyls" to remove aluminum hydride The TNHA feed consisted of 300 grams of TNHA, 30 grams of cyclooctane to use as a gas chromatograph standard, and 10 grams of 1-octene to help cut the viscosity. The 1-octene feed consisted of 500 mL of 1-octene and 1 mL of a 0.01284 gram Ni/mL of nonane solution. The Ni catalyst was 10 percent by weight Ni octanoate dissolved in mineral spirits. The Pb reagent used was 24% by weight Pb hexanoate in mineral spirits. The Pb solution was diluted with heptane to form a 0.1138 gram Pb/mL solution.

The 1-octene/Ni feed was pumped into the reactor via a metering pump. The TNHA feed was also fed into the reactor via a metering pump. There was an in line mixer right after the TNHA inlet to help insure good mixing. The reactor was a 3/8 inch stainless steel tube which was jacketed with a PAO bath. The tube was 15 inches long. The tube was packed with 100 mesh glass beads to insure plug flow. The reaction solution was sampled directly after leaving the back-displacement reactor. A 10 port 2-way valve was used which allowed for consistent sampling with heptane and nitrogen purge through the sample loop to insure that all reactants were collected.

The reaction mixture was then fed to a 1/16 inch tee at which point the Pb kill solution was added. The Pb solution was added via a syringe pump. The reaction solution was filtered and then passed through a PAO jacketed ¼ inch reaction tube. The tube was 24 inches long and was packed with 100 mesh glass beads After passing through the Pb reaction tube, the reaction solution was sampled again using another 10 port 2-way valve. The reaction solution was then collected in a 1-liter bomb.

Flow rates were set to achieve the following conditions:

| | |
|---|---|
| TNHA = | 0.38 g/min |
| 1-octene = | 1.57 g/min |
| Mole ratio of = Olefin/Aluminum Alkyl | 11.9 |
| Ni concentration = | 29 ppm |
| Pb concentration = | 242 ppm |
| Mole ratio of Pb/Ni = | 2.3 |

After the back-displacement reaction the conversion of hexyl groups to 1-hexene was 48.5 percent with a 1-hexene purity of 99.2 percent.

After the lead kill reaction the conversion was 57.9 percent with a 1-hexene purity of 99.4 percent.

What is claimed is:

1. A continuous process for preparing an alkyl aluminum compound from an internal olefin, said process comprising:

(a) continuously feeding (i) a linear internal olefin containing 4 to about 30 carbon atoms or a mixture of such internal olefins, (ii) a trialkyl aluminum, the mole ratio of said linear internal olefins to said trialkyl aluminum being about 1–50:1, and (iii) a catalytic amount of an isomerization catalyst to a reaction zone so as isomerize the internal olefinic double bond to form at least some linear 1-olefin which displaces alkyl groups from said trialkyl aluminum and forms an alkyl aluminum compound wherein at least one of the alkyl groups bound to aluminum is a linear alkyl derived from said linear 1-olefin, and (b) continuously removing olefin formed by the displaced alkyl groups and reaction mixture containing said alkyl aluminum compound from the reaction zone.

2. The process according to claim 1 wherein said reaction zone is a single reactor.

3. The process according to claim 1 wherein said reaction zone comprises a plurality of reactors in series.

4. The process according to claim 1 wherein said reaction zone comprises a plurality of stirred tank reactors in series.

5. The process according to claim 4 wherein additional isomerization catalyst is fed to one or more of the subsequent reactors.

6. The process according to claim 1 wherein said catalyst is an isomerization/displacement catalyst.

7. The process according to claim 4 wherein said catalyst is an isomerization/displacement catalyst.

8. The process of claim 1 wherein said trialkyl aluminum contains less than about 1.0 weight percent of aluminum hydride impurity and said catalyst is a nickel-containing isomerization/displacement catalyst.

9. The process of claim 8 wherein the nickel-containing catalyst is selected from nickel(II) salts, nickel(II) carboxylates, nickel(II) acetonates, nickel(0) complexes and mixtures thereof.

10. The process of claim 9 wherein the nickel-containing catalyst is selected from nickel bis-1,5-cyclooctadiene, nickel acetate, nickel naphthenate, nickel octanoate, nickel 2-ethylhexanoate and nickel chloride 11. The process of claim 8, wherein said catalyst is present in an amount of from about 0.01 to 5.0 mole percent of the trialkyl aluminum, said linear internal olefin is an n-hexene, and said trialkyl aluminum is tri-n-propylaluminum.

12. The process of claim 11 wherein said catalyst is nickel octanoate nickel acetate, nickel naphthenate, or nickel 2-ethylhexanoate.

13. The process of claim 4 wherein said trialkyl aluminum contains less than about 1.0 weight percent of aluminum hydride impurity and said catalyst is a nickel-containing isomerization/displacement catalyst.

14. The process of claim 13 wherein the nickel-containing catalyst is selected from nickel(II) salts, nickel(II) carboxylates, nickel(II) acetonates, nickel(0) complexes and mixtures thereof.

15. The process of claim 14 wherein the nickel-containing catalyst is selected from nickel bis-1,5-cyclooctadiene, nickel acetate, nickel naphthenate, nickel octanoate, nickel 2-ethylhexanoate and nickel chloride.

16. The process of claim 13 wherein said catalyst is present in an amount of from about 0.01 to 5.0 mole percent of the trialkyl aluminum, said linear internal olefin is an n-hexene, and said trialkyl aluminum is tri-n-propylaluminum.

17. The process of claim 16 wherein said catalyst is nickel octanoate, nickel acetate, nickel naphthenate or nickel 2-ethylhexanoate.

* * * * *